United States Patent [19]

Cramer et al.

[11] Patent Number: 5,020,089

[45] Date of Patent: May 28, 1991

[54] X-RAY EXAMINATION INSTALLATION WITH COORDINATED POSITIONING OF THE IMAGING SYSTEM AND THE PATIENT SUPPORT MECHANISM

[75] Inventors: Bernhard M. Cramer, Wuppertal; Erhard Jenner, Hessdorf; Wolfgang Minderle, Neustadt A.D. Aisch, all of Fed. Rep. of Germany

[73] Assignee: Siemens Aktiengesellschaft, Munich, Fed. Rep. of Germany

[21] Appl. No.: 420,914

[22] Filed: Oct. 13, 1989

[30] Foreign Application Priority Data

Oct. 25, 1988 [EP] European Pat. Off. ........ 88117778.6
Feb. 10, 1989 [EP] European Pat. Off. ........ 89102330.1

[51] Int. Cl.[5] .......... H05G 1/02

[52] U.S. Cl. .......... 378/196; 378/195; 378/198; 378/209

[58] Field of Search .......... 378/195, 196, 197, 198, 378/208, 209

[56] References Cited

U.S. PATENT DOCUMENTS

| | | | |
|---|---|---|---|
| 2,841,714 | 7/1958 | Vaughn | 378/196 |
| 3,215,835 | 11/1965 | Mueller | 378/196 |

FOREIGN PATENT DOCUMENTS

| | | |
|---|---|---|
| OS2356276 | 7/1974 | Fed. Rep. of Germany . |
| 1539969 | 9/1968 | France . |
| 2247954 | 5/1975 | France . |
| 2464057 | 3/1987 | France . |

*Primary Examiner*—Carolyn E. Fields
*Assistant Examiner*—David P. Porta
*Attorney, Agent, or Firm*—Hill, Van Santen, Steadman & Simpson

[57] ABSTRACT

An x-ray examination installation includes an imaging system having components disposed on opposite sides of a patient on a patient support table. Positioning of the imaging system is coordinated with positioning of the patient support system in that the components of the imaging system are automatically moved, upon positioning of the patient support system, in a direction opposite to the movement of the patient support table. The range of adjustment of the patient support table can be sub-divided into ranges to which separate switching stages are allocated, so that the movement of the imaging system in a direction opposite to movement of the patient support table occurs only within predetermined ranges, so that such movement is not effected when the patient support table is adjusted within a central range.

7 Claims, 2 Drawing Sheets

X-RAY EXAMINATION INSTALLATION WITH COORDINATED POSITIONING OF THE IMAGING SYSTEM AND THE PATIENT SUPPORT MECHANISM

BACKGROUND OF THE INVENTION

1. Field of the Invention

The present invention is directed to an x-ray examination installation having an imaging system and a patient support system, both of which are adjustable in position.

2. Description of the Prior Art

X-ray installations are known wherein a patient being examined is supported on a table which is adjustable in two dimensions, and wherein the patient and the patient support table are surrounded by a C-arm, with opposite ends at which an x-ray source and an x-ray image intensifier are respectively mounted. Adjustment of the patient relative to the imaging system can be undertaken both by adjusting the position of the patient support table and by adjusting the position of the imaging system carried on the C-arm. The respective adjustments of these two systems are not coordinated with each other. This means that the alignment of the patient with respect to the imaging system must be accomplished by separate and individual adjustment of the position of the patient support table and of the imaging system.

SUMMARY OF THE INVENTION

It is an object of the present invention to provide an x-ray examination installation having an imaging system and a patient support system wherein adjustment of the position of the patient relative to the imaging system is simplified and can be accomplished faster than in known systems.

The above object is achieved in accordance with the principles of the present invention in an x-ray examination installation wherein control means is provided such that, given a manual adjustment of the patient support table, the imaging system is automatically moved in a direct opposite to the direction of movement of the patient support table. The positioning of the imaging system can be accomplished by a motor-driven adjustment mechanism with control circuitry which provides signals for operating the motor which follow the movement of the patient support table in an opposite direction. The two motions are coordinated, for example, so that given a dislocation of the patient support table in the longitudinal direction, an oppositely directed, motor-driven displacement of the imaging system takes place, thereby providing a rapid adjustment of the position of the patient relative to the imaging system.

In a further embodiment of the invention, the entire range of possible movement (adjustment) of the patient support table is sub-divided into a number of ranges, with a switching stage being allocated to each range, and the control means generates signals to effect an opposite movement of the imaging system only when the movement of the patient support table occurs in predetermined ranges. For example, a central region of movement of the patient support table can be selected wherein no automatic, oppositely directed adjustment of the imaging system occurs. When the patient support table is moved out of this central region, the aforementioned oppositely directed adjustment of the imaging system occurs.

In a further modification of this embodiment, each of the ranges may have a speed of movement assigned thereto with the speeds changing symmetrically on both sides of the central region. When the patient support table is manually moved to a first range at one side of the central region, for example, the adjustment speed for the oppositely directed movement of the imaging system will be undertaken at a first, relatively low speed, and as further ranges are transgressed, i.e., as the patient support table is moved farther from the central region, the speed of movement of the oppositely directed adjustment of the imaging system is increased to a second, higher speed.

DESCRIPTION OF THE PREFERRED EMBODIMENTS

Figure 1:
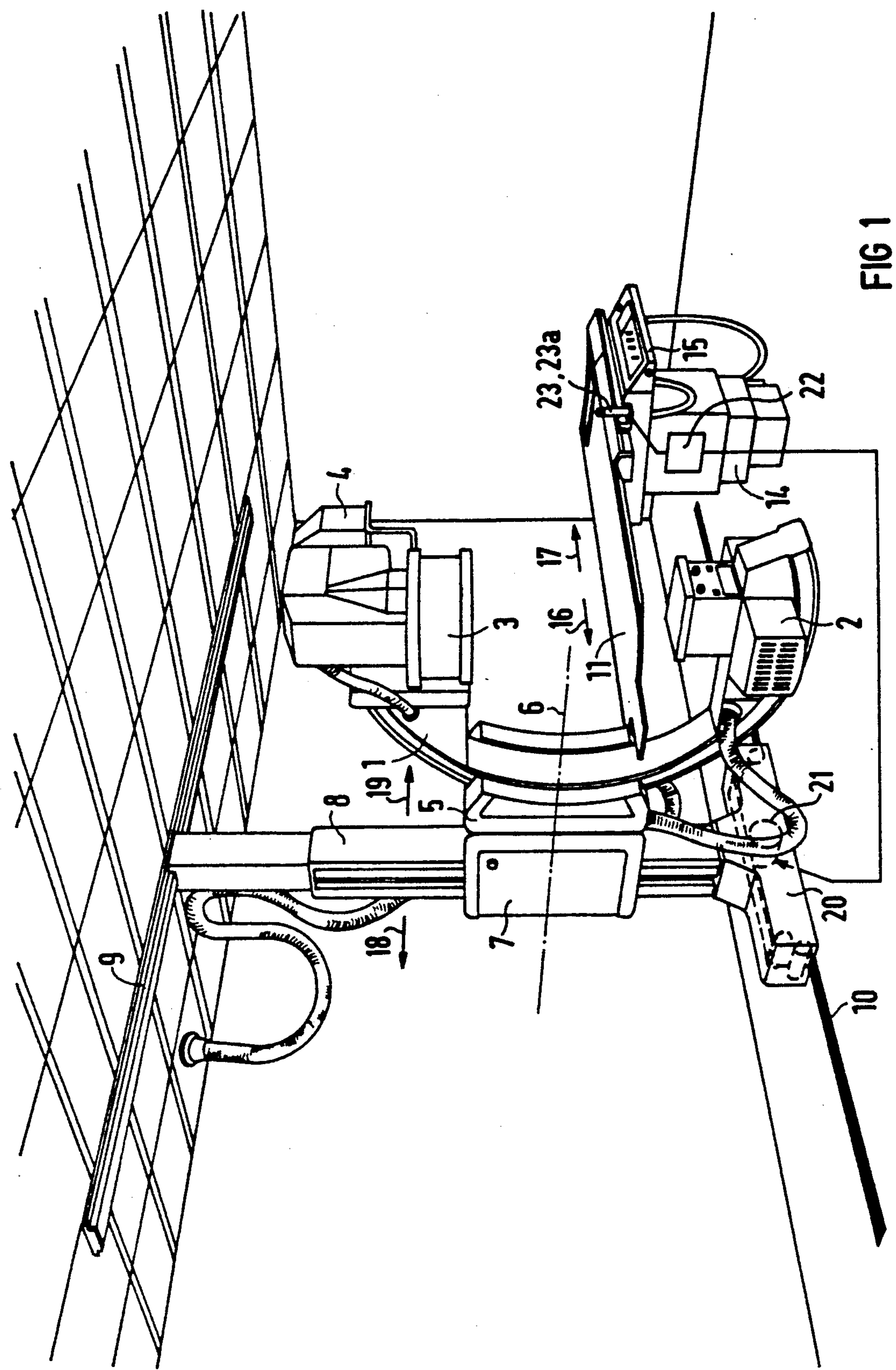
FIG. 1 is a perspective view of an x-ray examination installation constructed in accordance with the principles of the present invention.

An x-ray eXamination installation constructed in accordance with the principles of the present invention is shown in FIG. 1, which includes a C-arm 1 having opposite ends at which an x-ray source 2 and an x-ray image intensifier 3 are respectively mounted, with a single-frame photographic camera 4 and a video camera (not visible in FIG. 1) following the x-ray image intensifier 3. The C-arm 1 and the components mounted thereon form an imaging system, which is adjustable around the circumference of the C-arm 1 by a holder 5. The holder 5 is mounted to a carriage 7 so as to be pivotable around a horizontal axis 6, and the carriage 7 is seated on a vertical column 8 so as to be vertically adjustable. The vertical column 8 is longitudinally displaceable, together with the carriage 7, the holder 5 and the imaging system, along a ceiling rail 9 and a floor rail 10 extending parallel to each other, and parallel to the longitudinal axis of a patient support table 11. The C-arm 1 partially surrounds the patient support table 11. The patient support table 11 is adjustable in height by means of a pedestal or base 14, on which a control panel 15 is mounted. The patient support table 11 can be manually adjusted in the longitudinal direction as indicated by arrows 16 and 17, and can also be adjusted in a transverse direction, perpendicular to and in the same horizontal plane as, the longitudinal direction. Movement of the patient support table 11 is accomplished manually by a handle 23*a*.

Adjustment of the column 8 along the rails 9 and 10 is indicated by the arrows 18 and 19.

A motor 21 is provided in a base 20 of the column 8 for adjusting the position of the column 8 in the directions described above. The motor 21 is driven by a motor control 22, to which a transmitter 23, contained in the handle 23*a*, is connected. The transmitter 23 supplies an electrical signal to the motor control 22 corresponding to the movement (direction and magnitude) of the patient support table 11 in the direction of the arrows 16 and 17.

If the patient support table is manually displaced in the direction of the arrow 16, for example, the signal from the transmitted 23 causes the motor control 22 to operate the motor 21 so that the column 8, and the imaging system carried thereon, are moved in the direction of the arrow 19. If the patient support table 11 is adjusted in the direction of the arrow 17, an oppositely directed, motor-driven adjustment of the column 8, and the imaging system carried thereon, automatically ensues in the direction of the arrow 18. Adjustment of a patient lying on the patient support table 11 with respect to the imaging system can thus be accomplished very quickly and simply by the automatic, oppositely directed adjustment as described above.

The automatic, oppositely directed adjustment of the column 8 and the imaging system following adjustment of the patient support table 11 has been described in connection with FIG. 1 with respect to only one dimension. The oppositely directed adjustment can also be provided in the same manner in a second dimension, perpendicular to the first dimension. If, for example, the patient support table 11 is moved along the axis 6 in a direction toward the column 8, adjustment of the imaging system along the axis 6 away from the column can automatically ensue, and vice versa. For this purpose, the holder 8 can be connected to the carriage 7 by means of a further motor (not shown) operable to move the holder 5 along the axis 6.

As described, the automatic, oppositely directed adjustment of the imaging system relative to the patient support table 11 ensues on the basis of the signal supplied by the transmitter 23 which corresponds to the direction of movement of the patient support table 11. It is also possible, however, to move the patient support table 11 by a motor, which can be manually controllable, in which case the transmitter 23 will provide control signals derived from the manual motor controls.

Figure 2:
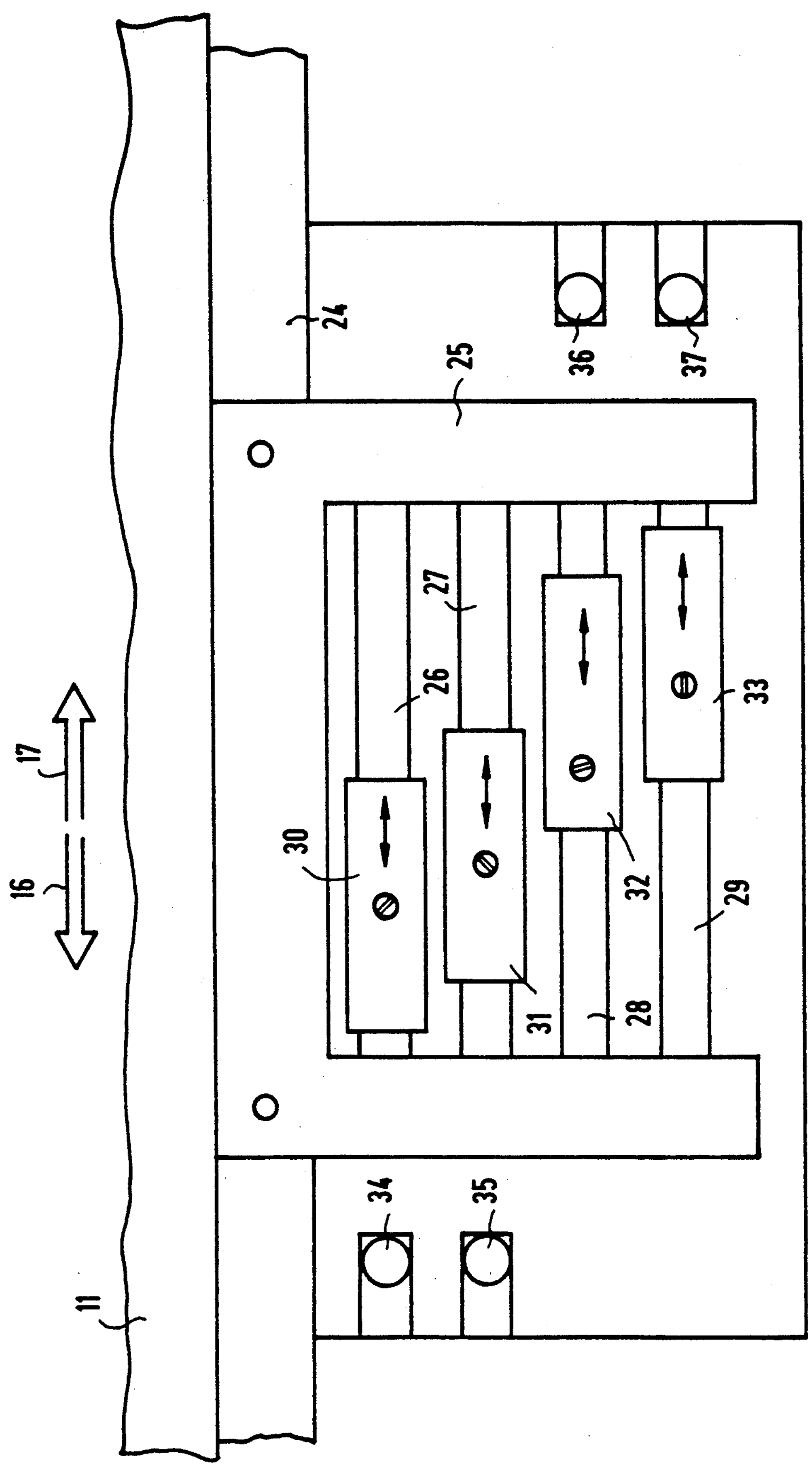
FIG. 2 is a plan view of a portion of the adjustment controls for the x-ray examination installation shown in FIG. 1.

A switch actuator is shown in plan view in FIG. 2, by means of which the total adjustment range of the patient support table 11 can be divided into a plurality of sub-ranges. The switch actuator can be attached to the accessories rail 24 of the patient support table 11, which is already present in most installations. The switch actuator includes a holder or frame 25 having a plurality, such as four, of parallel guide rods 26, 27, 28 and 29. The guide rods have respective adjustable actuation elements 30, 31, 32 and 33, each of which is slidable along the guide rod on which it is mounted in the direction of the double arrow, and once positioned on the guide rod, the actuation element is then made immoveable by turning a set screw. Each guide rod is aligned so that the actuation element thereon interacts with one of a plurality of limit switches 34, 35, 36 and 37. The frame 25 and the guide rods are positioned above the limit switches so as not to interact therewith; only the actuation element on each guide rod can actuate the limit switch aligned therewith. The limit switches 34 through 37 are each connected to the motor control 22 and, when actuated, cause the motor control 22 to operate the motor 21 in a defined manner, as described below.

When the patient support table 11 is adjusted within a central region, within which none of the limit switches 34 through 37 is actuated by an actuation element 30 through 33, the imaging system remains at rest, i.e., is not adjusted in a direction opposite to the direction of movement of the patient support table 11. When the central region of the patient support table 11 is transgressed as the patient support table 11 is moved to one side or the other of the central region, one of the actuation elements will engage its associated limit switch. In the example shown in FIG. 2, if the patient support table 11 were moved in the direction of the arrow 16, the actuation element 30 would engage the limit switch 34. If the patient support table 11 were moved in the opposite direction 17, the actuation element 33 would engage the limit switch 37. When either the limit switch 34 or the limit switch 37 is actuated, the motor control 22 is activated so as to operate the motor 21 at a first, low speed, so that the imaging system is accordingly moved in a direction opposite to the direction of movement of the patient support table 11, at a relatively low speed. If the original direction of movement of the patient support table 11 were in the direction of the arrow 16, and if movement of the patient support table 11 in that direction were continued, the actuation element 31 would subsequently engage the limit switch 35. Similarly, if the original direction of movement of the patient support table 11 had been in the direction of the arrow 17, and if movement of the patient support table 11 in this direction were continued, the actuation element 32 would engage the limit switch 36. If either of the limit switches 35 or 36 is actuated, the motor control 22 is caused to operate the motor 21 at a second, higher speed. This results in the imaging system being moved in a direction opposite to the direction of movement of the patient support table 11 at a speed which is higher than the speed with which the imaging system was moved when the patient support table 11 was in the regions immediately adjacent the central region.

The overall range of movement of the patient support table 11 is thus sub-divided into five regions, a central region with two regions on each side thereof, with each region beyond the central region having a limit switch and an actuation element associated therewith. The size of each of the regions can be set by positioning the respective actuation elements 30 through 33 along the guide rods 26 through 29. If movement of the patient support table 11 takes place within the central region, no following movement of the imaging system occurs. If the patient support table 11 is moved in either direction from the central region into one of the immediately adjacent regions, the imaging system will be moved in the opposite direction at a low speed. If movement of the patient support table 11 continues beyond the immediately adjacent regions, the oppositely directed movement of the imaging system takes place at a higher speed.

Although modifications and changes may be suggested by those skilled in the art, it is the intention of the inventors to embody within the patent warranted hereon all changes and modifications as reasonably and properly come within the scope of their contribution to the art.

We claim:

1. An x-ray examination installation comprising:

a support table adapted to support a patient;

imaging means adapted for irradiating said patient with x-rays while on said support table and for generating an x-ray image of said patient;

motor-driven means for positioning said imaging means;

means for manually adjusting the position of said support table having a total range of movement along an axis, and including means for dividing said total range of movement into a plurality of sub-ranges and for operating said motor-driven means only in selected sub-ranges; and control means connected to said means for manually positioning said patient support table and to said motor driven means for positioning said imaging means for operating said motor-driven means to move said imaging means in a direction opposite to movement of said patient support table.

2. An x-ray examination installation as claimed in claim 1, wherein said patient support table has a longitudinal axis, and wherein said motor-driven means includes a vertical column to which said imaging means is attached and motor-driven means for moving said column and said imaging means attached thereto along said longitudinal axis of said patient support table.

3. An x-ray examination installation as claimed in claim 1, wherein said means for dividing is a means for dividing said total range of movement into a central sub-range and a plurality of sub-ranges on opposite sides of said central range and wherein no movement of said motor-driven means is caused by said control means in said central region.

4. An x-ray examination installation as claimed in claim 1, wherein said means for dividing is a means for dividing said total range of movement into a plurality of adjustable sub-ranges.

5. An x-ray examination installation as claimed in claim 1, wherein said control means further comprises means for operating said motor-driven means at different speeds in different sub-ranges.

6. An x-ray examination installation as claimed in claim 5, wherein said means for dividing is a means for dividing said total range of movement into a central sub-range and into first sub-ranges immediately adjacent opposite sides of said central sub-range and wherein said means for controlling includes means for operating said motor-driven means at a first speed in said first sub-ranges and at a second speed beyond said first sub-ranges.

7. An x-ray examination installation as claimed in claim 6, wherein said second speed is higher than said first speed.

* * * * *